United States Patent [19]

Dorwart, Jr. et al.

[11] 4,141,856
[45] Feb. 27, 1979

[54] REFERENCE MATERIAL FOR ESTABLISHING ANION CONCENTRATIONS IN ANALYTICAL CHEMISTRY TESTS

[76] Inventors: William V. Dorwart, Jr., 124 Maple Ave., Bala Cynwyd, Pa. 19004; Walter Brummund, Jr., 4033 Spruce St., Philadelphia, Pa. 19104

[21] Appl. No.: 794,864

[22] Filed: May 9, 1977

Related U.S. Application Data

[63] Continuation-in-part of Ser. No. 689,242, May 24, 1976, abandoned.

[51] Int. Cl.² .................. C09K 3/00; G01N 33/16; G01N 33/00
[52] U.S. Cl. .................. 252/408; 23/230 B; 195/103.5 R; 260/567.6 M; 423/371; 424/2; 424/329
[58] Field of Search .................. 424/329, 2; 260/567.6 M, 567.6 P; 252/408; 23/230 B; 195/103.5 R; 423/371

[56] References Cited

U.S. PATENT DOCUMENTS

| 2,295,504 | 9/1942 | Shelton | 424/329 |
|---|---|---|---|
| 2,666,009 | 1/1954 | Stayner | 424/329 |
| 3,272,701 | 9/1966 | Kaitz et al. | 424/329 |
| 3,466,249 | 9/1969 | Anderson | 252/408 |
| 3,506,828 | 4/1970 | Hansen et al. | 252/408 |
| 3,629,142 | 12/1971 | Marbach | 252/408 |
| 3,681,255 | 8/1972 | Wilfore | 252/408 |
| 3,746,511 | 7/1973 | Stookey et al. | 252/408 |
| 3,874,852 | 4/1975 | Hamill | 252/408 |
| 3,891,573 | 6/1975 | Stary et al. | 252/408 |
| 3,973,913 | 8/1976 | Louderdack | 252/408 |
| 3,992,149 | 11/1976 | Wang | 252/408 |
| 4,001,142 | 1/1977 | Turner | 252/408 |
| 4,007,008 | 2/1977 | Becker et al. | 252/408 |

OTHER PUBLICATIONS

Ph. D Thesis of Teeter, T. E., et al., "Reduction of Carbon Dioxide on Mercury Cathodes," University of Oregon, Eugene, Oregon (Jun. 1954).

Primary Examiner—Richard E. Schafer
Assistant Examiner—T. S. Gron
Attorney, Agent, or Firm—Caesar, Rivise, Bernstein & Cohen, Ltd.

[57] ABSTRACT

A composition for reconstituting blood serum to provide a control standard used in the analysis of blood serum, said composition comprising a quaternary ammonium carbonate or bicarbonate.

21 Claims, No Drawings

REFERENCE MATERIAL FOR ESTABLISHING ANION CONCENTRATIONS IN ANALYTICAL CHEMISTRY TESTS

This application is a continuation-in-part of Application Ser. No. 689,242, filed May 24, 1976, now abandoned.

This invention relates to a laboratory standard material, and more particularly, to a stable blood serum reference standard and to a method of preparation and use thereof.

Various types of apparatus have been developed in recent years for the automatic analysis of human blood serum, which apparatus are capable of making rapid simultaneous analytical determinations on a precise quantitative basis of various components of each of a series of blood serum samples successively introduced into the apparatus. Biochemical determinations may be made, for example, by such apparatus, of the following constituents of the blood serum samples: albumin, alkaline phosphatase, bilirubin, calcium, chloride, cholesterol, carbon dioxide content, creatinine, glucose, lactic dehydrogenase, inorganic phosphorus, potassium, sodium, total protein, transaminase, urea nitrogen, uric acid and creatine phosphokinase.

In order to calibrate the apparatus of the type for making these determinations, a reference standard blood serum sample is used whose constituents have precisely predetermined values. It is necessary for such reference standard serums to be capable of being stored for long periods of time without deterioration, and for that reason, it has been the practice to freeze-dry or lyophilize them. It has also been the prior art practice to reconstitute the reference standard serum before use by means of, for example, a separate aqueous solution containing ammonium bicarbonate to restore the carbon dioxide that has been lost in the blood serum during the lyophilizing process. Examples of reconstituting solutions that have been used in the prior art can be found in U.S. Pat. Nos. 3,466,249 and 3,629,142.

Although the composition of this invention has as its primary purpose the reconstitution of lyophilized blood serum to return to the serum a known quantity of carbonate or bicarbonate so that the apparatus can be calibrated for determining the amount of carbon dioxide in the blood, the composition of this invention is useful for various other chemical analyses. As is well known, secondary reference materials serve two important functions in analytical chemistry laboratories. They are used as standards for calibrating instruments, and they are used to check the accuracy and precision of the assay results. These secondary reference materials usually contain multiple substances, so that just one solution can be used for most of the assays done by the laboratory. Moreover, multiple-substance quality control reference materials are essential for use with multiple assay chemistry analysers.

In compounding these materials, there is often difficulty in fixing the concentration of one or more anions at a desired level in the material without having the obligatory cations affect other laboratory assays. One very important example of the problem is that set forth above, namely, fixing the total carbon dioxide content (bicarbonate plus carbonate) in quality control or reference serums used in clinical chemistry laboratories.

Bicarbonate salts which have been used to fix total carbon dioxide content in these serums are the bicarbonates of sodium, potassium, lithium, rubidium, TRIS (tris(hydroxymethyl) aminomethane) and ammonia. Sodium, potassium and lithium bicarbonates are unsuitable for the purposes described because sodium, potassium and lithium are important analytes, and because lithium is also used as an internal standard in the common flame photometric determination of sodium and potassium. Rubidium bicarbonate (at a concentration of 25mM) is unsuitable as a total carbon dioxide reference material because it elevates sodium determinations by about 2mM, possibly through a matrix effect in the flame photometer.

It has been found that the TRIS bicarbonate-based reference material disclosed in aforementioned U.S. Pat. No. 3,629,142 has a major shortcoming for reference purposes because it depresses the urea result (urease-Berthelot method) by about 15 percent, and enhances protein results by about 10 percent. The effect of TRIS on the urea results may be related to interference with the Berthelot reaction by a number of nitrogen-containing compounds, as reported by Gips and Reitsema, "Clin. Chem. Acta.", 33, 257 (1971). Ammonium bicarbonate-reconstituted reference materials, which are the most widely used total carbon dioxide reference materials, are useless for most urease-based procedures for determining urea, because of ammonium ion interference. The ammonium ion also severely disturbs specific electrodes employed for determining potassium.

Thus, the presently available total carbon dioxide reference materials are unsuitable as reference materials for several other important analytical chemistry assays. A laboratory performing total carbon dioxide measurements in addition to the assays which are interfered with by the above mentioned total carbon dioxide reference materials must prepare two different lyophilized serum references, that is, one reconstituted with water and the other reconstituted with a bicarbonate solution. This duplication is burdensome, especially if a single multiple-channel instrument is performing the above tests, since twice the usual number of standards and/or quality controls are required.

We have found that duplication is eliminated and that expenses are reduced when the reference materials of this invention are used as a total carbon dioxide reference, because the reference materials of the invention affect the level of no analyte of clinical chemical interest, save total carbon dioxide. An additional advantage of the invention is the direct comparability of data for different laboratories participating in a regional quality control program (in which the participating laboratories all use the same lyophilized serum pool), even if some of the laboratories use water-reconstituted instead of bicarbonate-reconstituted serum controls.

This invention comprises the use of a salt selected from the class of compounds described below, for use in fixing the concentration of an anion in analytical chemistry reference materials, and which, when used for this purpose, gives no other interference with other chemical assays. The materials of this invention, which we have used to standardize and monitor the quality of clinical chemistry assays, contain salts of quaternary ammonium compounds. Such compounds contain at least one tetrasubstituted nitrogen wherein certain of the substituent groups may be joined to form heterocycles, for example, 1-alkylpyridine and 1,1-dialkylpiperidine, or polymerized via linkage of the substituent groups. The substituent groups should exhibit minimal interference in clinical determinations such as those set forth hereinafter, and the compounds themselves should be essentially free of contaminants, e.g., sodium, potassium, chloride, calcium, iron and ammonium. The amounts of these ions respectively which could be present in a commercially practicable diluent are no more than 2 millimolar, 0.25 millimolar, 3.0 millimolar, 0.5 milligrams/100 milliliters, 3.0 micrograms/100 milliliters and 3.0 micrograms/100 milliliters, with the preferred values being, respectively, 1.0 millimolar, 0.2 millimolar, 2.0 millimolar, 0.2 milligrams/100 ml, 2.0 micrograms/100 milliliters and 2.0 micrograms/100 milliliters, which would interfere in such determinations.

Additionally, the substituents should not render the compounds so insoluble that particles thereof would disrupt optical measurement of the reference material. Most importantly, no substituents should introduce significant buffering capacity into the compounds. Exemplary substituent groups are the saturated or unsaturated heterocycles such as furan or tetrahydrothiophen radicals, cycloalkenyl groups such as phenol, cycloalkyl groups, such as cyclohexyl and cyclopropyl, and branch chain or normal alkyls or alkenyls including methyl, ethyl, propyl, butyl, pentyl, octyl, hexene, isobutyl and neohexyl. Further, any of the foregoing groups can be additionally substituted with or contain oxygen or thioethers, ketones, esters, halides, nitro or hydroxyl. However, it is preferred to employ the branch chain or normal alkyls or alkenyls as these are the most chemically inert substituent groups, with the most preferred being methyl. Each of the four substituent groups can be the same as or different from one or more of the remaining groups.

The anions which may be employed to form the quaternary ammonium salts may be, for example, carbonate, bicarbonate, mixtures of carbonate and bicarbonate, halide and any other anion of clinical interest. The preferred anion is carbonate or bicarbonate.

Using the preferred tetrasubstituted ammonium bicarbonate or carbonate salts of the present invention, the total carbon dioxide level in a serum or other biological fluid control may be conveniently adjusted to any desired level, without interfering with other chemistry procedures. Assays in which no interferences were found include the following assays: sodium, potassium, chloride, glucose, blood urea nitrogen, creatinine, calcium, phosphorus, total protein, alkaline phosphatase, total bilirubin, iron, total iron binding capacity, cholesterol, triglycerides, uric acid, alanine aminotransferase, lactate dehydrogenase, hydroxybutyrate dehydrogenase, gamma-glutamyltransferase, lactic acid dehydrogenase, acid phosphatase, alkaline phosphatase, thyroid hormone uptake, total thyroid hormone and amylase. The bicarbonate materials add no color, so that they do not affect colorimetric determinations. They do not cause precipitation of any of the other components of the control material which could result in the plugging of instruments. In addition, the pH of the control solution can be adjusted by varying the ratio of bicarbonate to carbonate in the tetrasubstituted ammonium salt. An important feature of the present invention is that the tetrasubstituted ammonium ion has no buffering capacity, and as a result, only minimal amounts of such ions are required in fixing the carbon dioxide content of the reference material, regardless of the pH. TRIS, on the other hand, is a buffer at pH 8, and therefore TRIS bicarbonate solutions contain more TRIS than bicarbonate, since some of the TRIS is uncharged. Further, the presence of buffering capacity will interfere with titrimetric methods for determining $CO_2$.

EXAMPLE 1

By way of example of the application of the present invention, the synthesis and use of tetramethylammonium bicarbonate (TMA-$HCO_3$) as a total carbon dioxide content reference material is described below (see also the reaction scheme). A solution of analytically pure tetramethylammonium bromide of the desired concentration (for example, 0.15 M) was converted to tetramethylammonium hydroxide by passage through a chromatographic column containing a strongly basic exhange resin in the hydroxide form (step 1).

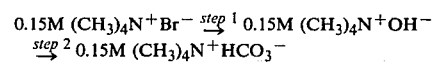

$0.15M\ (CH_3)_4N^+Br^- \xrightarrow{step\ 1} 0.15M\ (CH_3)_4N^+OH^-$
$\xrightarrow{step\ 2} 0.15M\ (CH_3)_4N^+HCO_3^-$ Conversion of the tetramethylammonium hydroxide to TMA-$HCO_3$ was accomplished by bubbling a stream of $CO_2$ gas into the stirred solution until a pH of 8 was obtained. The pH of the solution can be changed by changing the amount of $CO_2$ added to the solution. The TMA-$HCO_3$ solution was diluted to the desired total carbon dioxide content (for example 30mM). This TMA-$HCO_3$ solution was then used to reconstitute previously lyophilized serum controls. Alternatively, the TMA bicarbonate or carbonate salt may be added to the lyophilized serum control prior to its reconstitution with distilled water.

These TMA-$HCO_3$-reconstituted controls were then analyzed by known analytical chemistry procedures. Many such control serums so reconstituted were analyzed in parallel with controls reconstituted with only distilled water. No significant differences between these two controls was found for any of the assays in which the controls were used, which included those mentioned above.

In another application of our invention, we have found that other tetrasubstituted ammonium anion salts can be used in analytical chemical laboratories. For example, tetrasubstituted ammonium halide salts can be used as standards and controls in both clinical and toxicology laboratories. Like the tetrasubstituted ammonium becarbonate and carbonate salts, these salts add no color to reference materials to which they are added, so that they do not affect colorimetric determinations. They are chemically unreactive in other laboratory methods, and they do not cause precipitation of any of the other components of the control materials to which they may be added, which could result in the plugging of instruments.

EXAMPLE 2

Tetrabutyl ammonium bromide-reconstituted control serum is an application of our invention which may be used to fix the level of bromide in bromide assays. A solution of 30 mM tetrabutylammonium bromide was used to reconstitute lyophilized control serum, in a manner analogous to that used for the tetraalkylammonium bicarbonates. The resulting tetrabutylammonium bromide control material was then analyzed by known analytical chemistry procedures. These control serums were analyzed in parallel with controls reconstituted with distilled water only. No significant differences between these two controls was found for any of the assays in which the controls were used, except for the halide assays, in which the tetrabutylammonium bromide-reconstituted controls were elevated by an amount corresponding to 30mM bromide.

The tetrasubstituted ammonium anion salts of this invention are known in the art. However, these salts have not been used in the analytical chemistry procedures in which the salts of this invention are being used. The salts and their methods of production are disclosed in Czechoslovakian Pat. No. 157,000 and in U.S. Pat. Nos. 3,190,919, 3,579,581, 3,539,605 and 3,397,215. They are also disclosed in the literature in Mahajan and Rao, "Proton Magnetic Resonance and Internal Motions in some Tetramethyl Ammonium Compounds", J. Phys. C: Solid State Phys., Vol. 7, Great Britain (1974) and the Ph.D Thesis of Teeter, Truman E. entitled "Reduction of Carbon Dioxide on Mercury Cathodes", the University of Oregon, Eugene, Oreg., June 1954.

EXAMPLE 3

In order to show the efficacy of the quaternary ammonium carbonates and bicarbonates of this invention in adding carbon dioxide to a blood serum reference material, two samples from the same lot of lyophilized blood serum were taken. Each sample consisted of the amount of blood serum that could be lyophilized from 10ml of blood serum. 10ml of distilled water were added to the first sample, and the bottle containing the sample was agitated so that the serum would completely dissolve. The content of this sample was then analyzed with a conventional apparatus for analyzing blood serum.

The second sample of lyophilized blood serum was reconstituted by adding 10ml of 22mM tetramethylammonium bicarbonate. Here again, the mixture was slightly agitated so that the serum would be completely dissolved in the solution of tetramethylammonium bicarbonate. The second sample was then analyzed using the same apparatus as used on the first sample.

The following chart gives the results of the tests for the constituents tested, and also shows the normal range for the constituents.

| CONSTITUENTS | VALUE PRIOR TO ADDITION OF TETRAMETHYLAMMONIUM BICARBONATE | VALUE AFTER ADDITION OF TETRAMETHYLAMMONIUM BICARBONATE | NORMAL RANGE |
|---|---|---|---|
| Sodium | 150meq/l | 150meq/l | 138 – 146 |
| Potassium | 6.5meq/l | 6.14meq/l | 3.5 – 5.3 |
| Chloride | 107 mcq/l | 107meq/l | 97 – 108 |
| Carbon Dioxide | 3meq/l | 25meq/l | 24 – 32 |
| Glucose | 172mg/dl | 171mg/dl | 60 – 105 |
| Urea Nitrogen | 44mg/dl | 44mg/dl | 10 – 20 |
| Creatinine | 4.9mg/dl | 4.9mg/dl | 0.7 – 1.4 |
| Calcium | 11.9mg/dl | 12.0mg/dl | 8.5 – 10.5 |
| Phosphorus | 7.3mg/dl | 7.3mg/dl | 2.4 – 4.4 |
| Total Protein | 6.5mg/dl | 6.4gm/dl | 5.8 – 8.5 |
| Alkaline Phosphatase | 107IU/l | 109IU/l | 12 – 40 |
| Bilirubin | 3.6mg/dl | 3.6mg/dl | 0.2 – 1.2 |
| Iron | 198 μg/dl | 196 μg/dl | 70 – 200 |
| Iron Binding Capacity | 386 μg/dl | 412 μg/dl | 250 – 400 |
| Cholesterol | 153mg/dl | 150mg/dl | up to 260 (age dependent) |
| Triglycerides | 0.9meq/l | 0.88meq/l | up to 2.15 (age dependent) |
| Uric Acid | 9.1mg/dl | 9.0mg/dl | 3 – 8 |
| Aspartate Transaminase | 63IU/l | 61IU/l | 6 – 38 |
| Alanine Transaminase | 165IU/l | 166IU/l | 9 – 25 |
| Lactate Dehydrogenase | 737IU/l | 738IU/l | 140 – 270 |
| Creatine Kinase | 260IU/l | 274IU/l | 14 – 90 |
| Hydroxybutyrate Dehydrogenase | 587IU/l | 591IU/l | 110 – 230 |
| Gamma Glutamyl Transpeptidase | 26IU/l | 26IU/l | 4 – 40 |
| Amylase | 430U | 434U | 40 – 180 |

Notes:
IU/l = international units per liter
meq/l = milliequivalents/liter
mg/dl = milligrams/deciliter
μg/dl = micrograms/deciliter
gm/dl = grams/deciliter It is thus seen from a review of the foregoing test results that, with the exception of the carbon dioxide, the addition of the tetramethylammonium bicarbonate did not affect or interfere with the measurement of any of the other constituents of the blood serum or contribute any of the other constituents to the serum to change the concentration of the constituent in the serum. Insofar as the carbon dioxide is concerned, it can be seen from the foregoing analysis that the concentration of carbon dioxide had fallen to 3meq/l in the blood serum during lyophilization. This is from a normal range of 24 to 32meq/l. However, by mixing the lyophilized blood serum with the solution of tetramethylammonium bicarbonate, the concentration of carbon dioxide had risen to 25meq/l, which is within the normal range. Subsequent tests gave similar results.

The quaternary amines useful in this invention are all soluble in water. Additionally, when used with blood serum, they are also soluble in the serum. They are also soluble in the chemical mixtures used in the clinical tests. Naturally, the amine should not interfere in any clinical assay. The compositions containing the amines should be sterile. Sterility can be obtained by well known methods which will not affect the quaternary amines, for example, filtration of a solution of the amines through a filter which will retain particles the size of microorganisms.

Among the cations which can be used in forming the amines of this invention are the following:

trimethyl hydroxyethylammonium
dimethyl chloromethyl phenylammonium
tetraethylammonium
tetramethylammonium
tetrapropylammonium
tetrabutylammonium
N, N - dimethyl - N - ethyl - p - nitrophenylammonium
N, N - dimethyl - N - fluoromethyl - N - phenylammonium
N - cyclohexyl - N, N - dimethyl - N - isobutylammonium
N - ethyl - N - methylpiperidinium
N, N - dimethyl - N - ethyl - N - vinyl - ammonium
N, N - diethyl - N - (2 - methoxyethyl) - N - n - butylammonium
N- n - octyl - N, N, N - trimethylammonium
N, N, N, N', N', N' - hexamethylethylene diaminium
N - (2 -hydroxyethyl) trimethylammonium The anions which can be used are those specified above, which include carbonates, bicarbonates, a mixture of carbonates and bicarbonates, halides and any other anion of clinical interest.

In carrying out the method of this invention, the lyophilized serum is reconstituted with sufficient ammonium carbonate or bicarbonate to provide from about 10 to about 40meq/l of carbon dioxide in the reconstituted serum.

The reference serum of the invention may be prepared by mixing a solution of the tetrasubstituted ammonium salt of the desired final concentration with previously lyophilized blood serum. Alternatively, it may be prepared by adding a predetermined amount of tetrasubstituted ammonium salt to the blood serum prior to lyophilization of the serum. To prepare the reference serum of the invention by the latter method, the tetrasubstituted ammonium salt is added to pooled blood serum in sufficient amounts to provide the desired total $CO_2$ level in the reconstituted serum. For example, 1.0 ml of 0.4M tetraethyl ammonium bicarbonate is added to 10.0 ml of pooled blood serum. This mixture is then lyophilized by a known lyophilization process. The lyophilization serum can then be reconstituted prior to use by dissolving it in 10.0 ml of distilled water, whereupon it can be analyzed by known procedures.

Without further elaboration, the foregoing will so fully illustrate our invention, that others may, be applying current or future knowledge, readily adapt the same for use under various conditions of service.

What is claimed as the invention is:

1. A composition capable of use as a component of a clinical control material, comprising water and at least one water-soluble quaternary ammonium carbonate or bicarbonate, said composition including no substance which will affect assays for sodium, potassium, calcium, ammonium, chloride and iron ions.

2. The composition of claim 1 wherein the quaternary ammonium carbonate or bicarbonate is in concentration sufficient to provide a $CO_2$ concentration of from about 10 to about 40 meq./l.

3. The composition of claim 1 wherein the amount of sodium, potassium, calcium, ammonium, chloride and iron ions is, respectively, less than about 2 millimolar, about 0.25 millimolar, about 0.5 mg/100 ml, 0.5 µg./100 ml, 3 millimolar and 3 µg/100 ml.

4. The composition of claim 3 wherein the quaternary ammonium carbonate or bicarbonate is in concentration sufficient to provide a $CO_2$ concentration of from about 10 to about 40 meq./l.

5. The composition of claim 1 wherein the amount of sodium, potassium, calcium, ammonium, chloride and iron ions is, respectively, less than about 1 millimolar, 0.1 millimolar, about 0.2 mg/100 ml, 0.2 µg/100 ml, 2 millimolar and 2 µg./100 ml.

6. The composition of claim 5 wherein the quaternary ammonium carbonate or bicarbonate is in concentration sufficient to provide a $CO_2$ concentration of from about 10 to about 40 meq./l.

7. A sterile composition capable of use as a component of a clinical control material, comprising water and at least one water-soluble quaternary ammonium carbonate or bicarbonate.

8. The composition of claim 7 wherein the quaternary ammonium carbonate or bicarbonate is in concentration sufficient to provide a $CO_2$ concentration of from about 10 to about 40 meq./l.

9. A composition capable of use as a component of a clinical control material, comprising water and at least one water-soluble quaternary ammonium carbonate or bicarbonate, said composition including no substance which will affect assays for sodium, potassium, chloride, iron, phosphorus and calcium ions, urea, uric acid, creatinine, glucose, cholesterol, bilirubin, total protein, lactic acid dehydrogenase, amylase, acid phosphatase, alkaline phosphatase, thyroid hormone uptake and total thyroid hormone.

10. The composition of claim 9 wherein the quaternary ammonium carbonate or bicarbonate is in concentration sufficient to provide a $CO_2$ concentration of from about 10 to about 40 meq./l.

11. A composition capable of use as a clinical control material, consisting essentially of at least one water-soluble quaternary ammonium carbonate or bicarbonate and at least one animal body fluid.

12. A dry composition comprising at least one dried animal body fluid and at least one water-soluble quaternary ammonium carbonate or bicarbonate.

13. The composition of claim 12 wherein the amount of salt is known.

14. The composition of claim 12 wherein the body fluid is serum.

15. The composition of claim 12 wherein the composition is in vitro.

16. A composition for use as a clinical control serum, comprising at least one animal body fluid and at least one water-soluble quaternary ammonium carbonate or bicarbonate, wherein each tetrasubstituted group of said quaternary ammonium carbonate or bicarbonate is selected from the group consisting of saturated heterocycles, unsaturated heterocycles, cycloalkenyl groups, cycloalkyl groups, and branch chain lower alkyls, normal lower alkyls and normal lower alkenyls, with each of said lower alkyls and alkenyls having eight or less carbon atoms.

17. A method of making a clinical control serum which comprises mixing a water-soluble quaternary ammonium carbonate or bicarbonate and an animal body fluid, wherein each tetrasubstituted group of said quaternary ammonium carbonate or bicarbonate is selected from the group consisting of saturated heterocycles, unsaturated heterocycles, cycloalkenyl groups, cycoalkyl groups, and branch chain lower alkyls, normal lower alkyls and normal lower alkenyls, with each of said lower alkyls and alkenyls having eight or less carbon atoms.

18. A method for making a clinical control material which comprises mixing a quaternary ammonium carbonate or bicarbonate and a dry animal body fluid.

19. A method for making a clinical control material which comprises mixing an aqueous solution of a water-soluble quaternary ammonium carbonate or bicarbonate and an animal body fluid and then lyophilizing the mixture.

20. The method of claim 19 wherein the lyophilized mixture is reconstituted in water and then assayed for at least one of its clinically significant components.

21. The method of claim 18 wherein the quaternary ammonium carbonate or bicarbonate is added in sufficient concentration to provide from about 10 to about 40 meq./l. of $CO_2$ in the mixture when the dry animal body fluid is reconstituted to its water content prior to being dried.

* * * * *